United States Patent
Broyles et al.

(10) Patent No.: US 6,714,628 B2
(45) Date of Patent: Mar. 30, 2004

(54) MARKING GRID FOR RADIOGRAPHIC IMAGING, AND METHOD OF MAKING SUCH A GRID

(75) Inventors: Mark Broyles, Plainville, CT (US); Hermann Kasper, Plantsville, CT (US); Kimberlee Olson, Torrington, CT (US)

(73) Assignee: Beekley Corporation, Bristol, CT (US)

( * ) Notice: Subject to any disclaimer, the term of this patent is extended or adjusted under 35 U.S.C. 154(b) by 0 days.

(21) Appl. No.: 10/074,943

(22) Filed: Oct. 29, 2001

(65) Prior Publication Data
US 2003/0081732 A1 May 1, 2003

(51) Int. Cl.$^7$ .................................................. H05G 1/28
(52) U.S. Cl. ........................ 378/164; 378/163; 378/205
(58) Field of Search ................................ 378/162, 163, 378/164, 205; 604/116, 180

(56) References Cited

U.S. PATENT DOCUMENTS

| | | | |
|---|---|---|---|
| 4,349,917 A | 9/1982 | Moore .......................... 378/24 |
| 4,583,538 A | 4/1986 | Onik et al. .................. 128/303 |
| 4,838,265 A | 6/1989 | Cosman et al. ............. 128/303 |
| 4,860,331 A | 8/1989 | Williams et al. ............ 378/163 |
| 4,918,715 A | 4/1990 | Krupnick et al. ........... 378/164 |
| 4,985,019 A | * 1/1991 | Michelson ................... 378/164 |
| 5,178,146 A | 1/1993 | Giese ........................ 128/653.2 |
| 5,242,455 A | 9/1993 | Skeens et al. .............. 606/130 |
| 5,260,985 A | 11/1993 | Mosby ........................ 378/164 |
| 5,306,271 A | * 4/1994 | Zinreich et al. ............. 378/164 |
| 5,368,030 A | 11/1994 | Zinreich et al. ......... 128/653.1 |
| 5,690,108 A | 11/1997 | Chakeres ................. 128/653.1 |
| 5,913,863 A | 6/1999 | Fischer et al. .............. 606/130 |
| RE36,461 E | * 12/1999 | Russell et al. .............. 378/163 |
| 6,122,541 A | 9/2000 | Cosman et al. ............. 600/426 |

* cited by examiner

Primary Examiner—Edward J. Glick
Assistant Examiner—Allen C. Ho
(74) Attorney, Agent, or Firm—Cummings & Lockwood

(57) ABSTRACT

A marking grid is provided for use in radiographic imaging, and a method is provided for manufacturing the marking grid. The marking grid is comprised of a radiolucent substrate with a pressure sensitive adhesive on one side, a plurality of parallel strips of radiopaque material fixed to the substrate on the side opposite the pressure sensitive adhesive, and apertures in the substrate between the parallel strips of radiopaque material. The substrate is provided on a releasable backing with a plurality of holes longitudinally spaced relative to each other, which can be used to register the position of the substrate in the equipment used to produce the marking grids.

34 Claims, 2 Drawing Sheets

MARKING GRID FOR RADIOGRAPHIC IMAGING, AND METHOD OF MAKING SUCH A GRID

FIELD OF INVENTION

The present invention relates generally to a marking grid for radiographic imaging and, more particularly, to a marking grid for use in computerized tomography.

BACKGROUND OF THE INVENTION

Marking grids are used during radiographic imaging to provide visual reference points on the radiographic image. For example, marking grids may be used to locate the position of internal body structures or tumors relative to the reference points on the radiographic image. To use a marking grid, the marking grid is placed on or adjacent to the patient's body while the radiographic image is taken. The marking grid creates lines or dots on the radiographic image which can be used as reference points to locate the position of body structures or tumors relative to the location of the marking grid on the patient. Marking grids are often used in computerized tomography (CT) scanning to produce reference points on the CT scan image.

Prior marking grids have been comprised of elongated radiopaque strips or members fixed to a substrate material. The substrate material in these devices has been in the form of sheets, generally without openings in the material. As a result, the marking grid must be moved to allow the radiologist to mark the patient's skin or to insert a surgical device such as a biopsy needle. This can require multiple scans of an area to locate the biopsy needle properly.

Some prior marking devices have partially addressed this problem by providing one or more holes for inserting biopsy needles through the marking device. For example, in U.S. Pat. No. 4,860,331 to Williams et al., a marking device is described in which the substrate is perforated with widely spaced, small diameter holes to permit insertion of biopsy needles. These holes are not always in the optimal position for insertion of a biopsy needle, and the holes do not provide an adequate area for a radiologist to place necessary markings on a patient's skin. As a result, the radiologist may have to move the marking grid for insertion of biopsy needles or marking the skin, which can result in inaccurate insertion or marking.

Accordingly, it is an object of the present invention to overcome one or more of the drawbacks or disadvantages of the prior art and to provide a marking grid for radiographic imaging that allows a radiologist to place markings on the patient's body or insert biopsy needles in the optimum desired location selected by the radiologist.

SUMMARY OF THE INVENTION

The present invention provides a marking grid for radiographic imaging that permits the radiologist to place markings on the patient's skin or insert a device such as a biopsy needle in an optimal location as selected by the radiologist. The marking grid is comprised of a substrate material that conforms to the patient's skin. The substrate material is substantially radiolucent. The back side of the substrate is coated with a pressure sensitive adhesive which is used to adhere the marking grid to the patient's skin. The marking grid can be provided on a plastic or wax coated backing.

The marking grid includes a plurality of parallel strips of a material that is at least partially radiopaque. The parallel radiopaque strips produce images, typically dots, on a radiographic image. The substrate defines elongated apertures between the strips of radiopaque material. Each aperture extends along substantially the entire length of the adjacent radiopaque strip(s).

The present disclosure also relates to an improved method for manufacturing marking grids. The substrate is provided on a releasable backing, and the releasable backing defines a plurality of holes longitudinally spaced relative to each other along at least one, and preferably both, marginal portions of the backing. The holes are engageable with means for driving the backing, such as the pins of rotatably-driven sprockets or a tractor-feed drive. Accordingly, the holes allow precise registration of the backing with a tool, such as a cutting tool for cutting the stretchable substrate, an application tool for applying glue or other adhesives to the substrate to secure the radiopaque strips thereto, or a printing tool for printing letters or other indicia on the substrate or the backing.

Among the advantages of the present invention is that the elongated apertures in the substrate allow a biopsy needle to be inserted into the patient in an optimal location without the need to remove or replace the marking grid. The present invention also provides the advantage of allowing the radiologist to place markings on a patient's skin without moving the marking grid.

A further advantage of the present invention is that the marking grid can be produced rapidly and inexpensively.

Other advantages of the marking grid of the present invention will become readily apparent in view of the following detailed description of preferred embodiments and accompanying drawings.

BRIEF DESCRIPTION OF THE DRAWINGS

So that those having ordinary skill in the art to which the subject invention appertains will more readily understand the subject invention, reference may be had to the drawings, wherein.

DETAILED DESCRIPTION OF THE PREFERRED EMBODIMENTS

The present invention is directed to a novel marking grid that provides reference marks on radiographic images of a patient's body, while allowing biopsy needles to be inserted or markings to be made on the patient's skin without removing the marking grid. Preferred embodiments of the invention are described below in conjunction with the drawings provided herein. The preferred embodiments disclosed herein are to be considered exemplary of the principles of the present invention to the embodiments described or illustrated. Various modifications will be apparent to those skilled in the art based on the teachings herein without departing from the scope or spirit of the invention disclosed herein.

Figure 1:
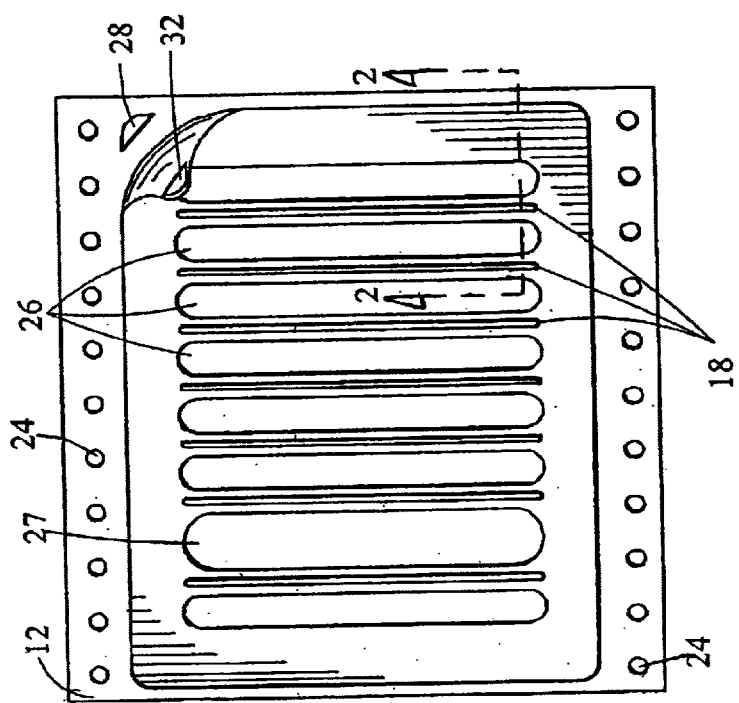
FIG. 1 shows a front view of a first embodiment of a marking grid on a backing material with a corner of the marking grid pulled away from the backing material.
Figure 2:
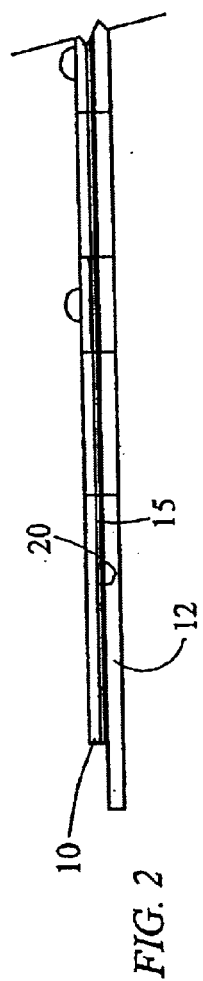
FIG. 2 shows a sectional side view of the marking grid shown in FIG. 1 through the section labeled 2—2 on FIG. 1.

Referring now to the figures wherein like reference numerals identify similar structural elements of the subject invention, as illustrated in FIG. 1 and FIG. 2, in one embodiment of the invention, the marking grid is comprised of a substrate 10 made of a material that is substantially radiolucent. The substrate may be flexible to permit it to be applied directly to a patient's body and conform to the shape of the patient's body. Plastic, paper, fabric or any other appropriate material known to those skilled in the art may be used for the substrate.

In a preferred embodiment of the invention, the substrate is comprised of an elastic material. The use of an elastic material allows the substrate to be conformed to the shape of the patient's body and remain fixed to the patient's body if the patient moves. In this preferred embodiment, an elastic material means a material that is sufficiently elastic to expand and contract with the surface of the skin to which it is attached. As may be recognized by those skilled in the pertinent art based on the teachings herein, the elastic substrate of the present invention may nevertheless undergo some degree of permanent deformation upon stretching with the patient's skin.

The elastic material should preferably be capable of stretching to between approximately 5% to approximately 50% of its original dimensions without rupture, and most preferably should be capable of stretching to at least approximately 30% of its original dimensions without rupture. A commercially available elastic material that may be used for the substrate is 3M Company's MSX-5190 (9907T) Nonwoven Medical Tape, which is capable of stretching to up to about 300% of its original dimensions. The 3M Nonwoven Medical Tape is an elastic, multi-layer polyurethane/rubber based non-woven material coated on one side with a hypoallergenic pressure-sensitive adhesive, and is provided on a bleached Kraft-Glassine paper.

It is preferred that the elastic material be capable of returning substantially to its original dimensions after imaging is complete. It is not required that the elastic material return to its original dimensions after use, however, as the marking grids are typically used only once, and a material that is permanently deformed by stretching may be used. In a preferred embodiment, after imaging is complete and the skin is allowed to relax, the elastic material returns to dimensions that are no more than about 105% of its original dimensions. The invention is not limited in this regard, however, and any appropriate elastic material may be used for the substrate.

As shown in FIG. 2, the back side 20 of the substrate 10 is coated with a pressure sensitive adhesive 15. Any appropriate pressure sensitive adhesive known to those skilled in the art may be used. The adhesive must be sufficiently adherent to hold the marking grid on the skin during the radiographic imaging process, while allowing removal from the patient with minimal discomfort at the end of the radiographic imaging process.

As shown in FIG. 1, the marking grid is provided on a backing 12. The backing 12 may be made from paper coated with wax or plastic, or from any other appropriate material that will allow easy removal of the marking grid from the backing without disrupting the pressure sensitive adhesive from the substrate. The backing has holes 24 on at least one side, and typically on two opposing sides, that can be used to feed the backing and substrate through manufacturing equipment or can be used in packaging to dispense the marking grids. The holes 24 are preferably spaced at regular intervals.

In a preferred embodiment, the backing 12 has a cut out portion 28 underlying a portion of the substrate 10. The cut out portion may be generally round, oval or crescent shaped, and can be die cut from the backing. The invention is not limited in this regard, however, and any desired shape may be used. The cut out portion 28 conforms generally with the shape of the corner of the marking grid. In use, the cut out portion 28 remains adhered to the underside of the corner of the marking grid when the marking grid is removed from the backing to form a gripping tab 32. The gripping tab enables the user to remove the marking grids from the backing without requiring the use of a fingernail or sharp instrument to peel the marking grid off of the backing. Also, the gripping tab allows the user to properly position the marking grid on the patient, as the gripping tab does not adhere to the user's finger. The gripping tab also allows for convenient removal of the marking grid from the patient after imaging because the gripping tab is not adhered to the patient's body.

Parallel strips 18 made of a material that is at least partially radiopaque are fixed to the substrate 10. The parallel strips 18 can be comprised of any material that is sufficiently radiopaque to produce visible marks on the radiographic image. For example, the strips may be comprised of a metal wire; of beads or strands of a homogeneous non-metallic material, such as polyvinyl chloride; or of a metal-compounded plastic material, such as nylon filled with tungsten carbide. Alternatively, the parallel strips may be comprised of fine particles of materials with a density greater than 1.0 g/cm$^3$. These particles could be metallic materials, such as, for example, tungsten or bismuth, or the particles could be non-metallic materials, such as, for example, barium sulfate or calcium carbonate. The particles may be dispersed in a carrier material, such as, for example, a hot melt or a glue, that is applied to the substrate. The particles are dispersed uniformly in the carrier material in a specific concentration to achieve the desired radiopacity. As shown in FIG. 1, the parallel strips 18 are preferably fixed to the front of the substrate 10. The parallel strips may be fixed to the substrate using any appropriate method known to those skilled in the art. In one embodiment of the invention, the parallel strips are fixed to the substrate using glue.

Between the parallel strips 18 of radiopaque material, the substrate defines a plurality of elongated apertures 26. The elongated apertures 26 extend laterally between the parallel strips 18 and extend substantially along the length of the parallel strips. In a preferred embodiment shown in FIG. 1, one of the apertures 27, and the corresponding distance between the parallel strips 18, is noticeably wider than all of the other apertures. This results in a wider distance between two of the reference points on the radiographic image between the parallel strips as compared to the rest of the reference points. The wider distance between points on the radiographic image may be used as a reference for determining the location of the marking grid relative to the image.

In use, the marking grid is removed from the backing and is placed on the patient's skin in the area of interest. For a CT scan, the marking grid is placed with the radiopaque strips substantially perpendicular to the plane of the scan. The marking grid is held in place by the pressure sensitive adhesive. A radiographic image, such as a CT scan, is taken through the area of interest. When a CT scan is taken, the radiopaque strips 18 produce reference marks on the image. The desired point of entry for the biopsy needle is determined from the radiograph. The apertures 26 in the marking grid provide spaces that allow the patient's skin to be marked with a felt pen or other appropriate marking implement in the precise location where the biopsy needle is to be inserted. The marking grid may be removed, the patient's skin sterilized, and the biopsy performed in the marked location. Alternatively, the biopsy may be performed with the marking grid in place.

The marking grid shown in FIG. 1 may be manufactured by obtaining a strip of substrate material that is coated on the back side with a pressure sensitive adhesive and is attached to a releasable backing. The releasable backing has holes on at least one side that are spaced equidistantly from each other. If desired, the releasable backing may have equidistantly spaced holes on two opposing sides as shown in FIG. 1. As discussed further below, the holes may be used to feed the substrate material and backing through the manufacturing equipment used to manufacture the marking grid. In addition, the holes may be used to register the location of the substrate in the manufacturing equipment.

To produce the marking grid shown in FIG. 1, the parallel strips 18 of radiopaque material are fixed to the front side of the substrate at predetermined locations. The holes 24 on the side of the releasable backing material are used to register the precise location of the substrate to ensure that the parallel strips are fixed to the substrate at the proper location, with the desired space between the parallel strips.

The substrate is cut to the desired shape, with apertures cut between the parallel strips. Cutting is typically performed using a die cutter that is set up to cut the substrate without cutting the releasable backing. The die cutter may be used to cut the portion of the releasable backing used for the gripping tab without cutting the substrate. Excess substrate material may be removed from the releasable backing and discarded. The holes in the releasable backing are used to register the precise location of the substrate in the cutting equipment to ensure that the substrate is cutting the correct locations. This allows reduction in the amount of substrate material that may be discarded and allows the cutting process to be performed rapidly, thereby reducing production costs.

Figure 3:
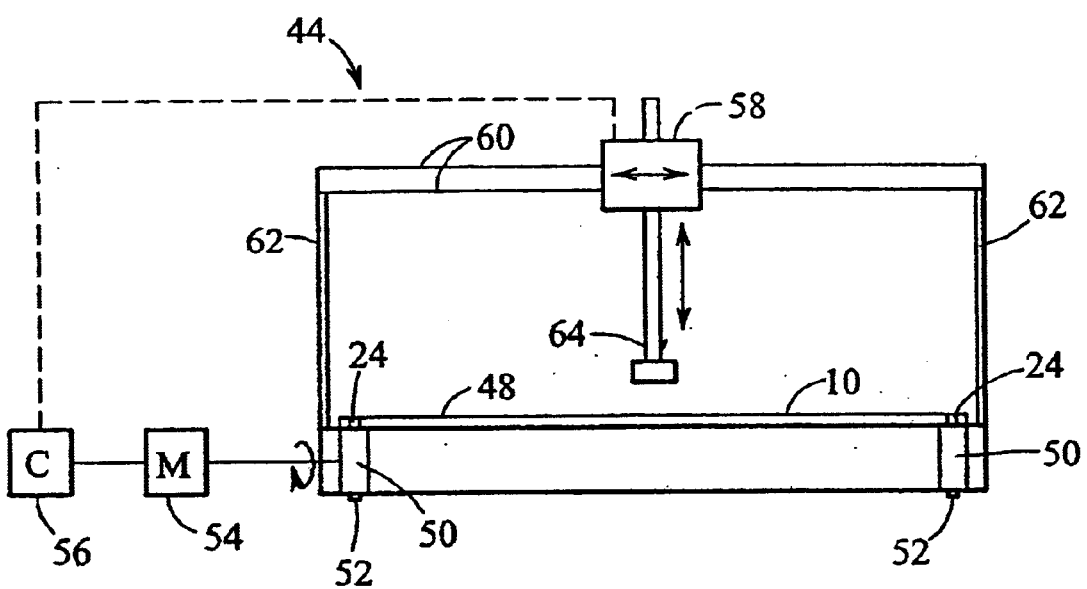
FIG. 3 is a somewhat schematic illustration of an apparatus for manufacturing the marking grids of the present invention.

Turning to FIG. 3, an exemplary apparatus for manufacturing the marking grid of the present invention is indicated generally by the reference numeral 44. The apparatus 44 includes a base 46 defining a work support surface 48. Drive means, such as sprockets 50, are rotatably mounted on the base 46 adjacent to the work support surface 48 and include a plurality of drive members, such as sprocket pins 52. As can be seen, the sprocket pins 52 are received within the apertures 24 of the releasable backing to engage and, in turn, drive the backing through the apparatus. A motor 54 is drivingly connected to the drive means 50, and a control unit 56 is electrically coupled to the motor to control the movement of the marking grid through the apparatus. A carriage 58 is drivingly mounted on a pair of ways or like supports 60 extending over the work support surface 48, and vertical supports 62 support the ways over the work support surface. A tool head 64 is mounted on the carriage and, as indicated by the arrows in FIG. 3, the tool head is movable toward and away from, or into and out of engagement with, the marking grid located on the work support surface 48. As also indicated by the arrows in FIG. 3, the carriage 58 is driven laterally along the ways 60 to position the carriage, and thus the tool head 64 relative to the work support surface. As indicated by the broken lines in FIG. 3, the carriage 58 and tool head 64 are electrically connected to the control unit 56 to drivingly control the position of the carriage and tool head relative to the work support surface and the marking grid located thereon.

Preferably, the tool head 64 is adapted to receive any of numerous different tools for manufacturing the marking grids of the present invention. For example, the tool head 64 is adapted to mount a dispensing tool of a type known to those of ordinary skill in the pertinent art for dispensing the radiopaque strips 18 onto the substrate 10. In addition, the tool head 64 is adapted to mount a cutting tool for cutting the peripheral portions of the substrate and cutting the elongated apertures and other portions of the substrate. Also, the tool head 64 is preferably adapted to mount a printing head for printing indicia or other markings on the substrate. Alternatively, different apparatus similar to that shown in FIG. 3 may be employed to perform one or more of these different operations on the marking grids of the present invention.

A significant advantage of the marking grid of the present invention is that the apertures 24 formed in the marginal portions of the releasable backing 12 allow precise registration between the tool head and both the backing and the substrate attached to the backing. Thus, the apertures 24 allow the radiopaque strips 18 to be rapidly and precisely applied to the substrate, and further, allow the elongated apertures 26 and 27 to be rapidly and precisely formed in the substrate.

As may be recognized by those skilled in the pertinent art based on the teachings herein, the drive means may take any of numerous different configurations that are currently, or later become known for driving the releasable backing or like substrates through computer controlled manufacturing apparatus of the type shown. For example, the drive means may take the form of a tractor feed drive, or may take the form of sprockets have other uniquely-shaped pins or other drive members, requiring any of numerous different aperture shapes or patterns formed in the marginal portions of the backing 12.

As may be further recognized by those of ordinary skill in the art based on the teachings herein, numerous other changes and modifications may be made to the above-described and other embodiments of the present invention without departing from its scope and spirit as defined in the appended claims. For example, the marking grid described herein may include any of numerous types of radiopaque or partially radiopaque materials, and a single marking grid can include any desired number of parallel strips. In addition, the spaces between the parallel strips and the sizes of the apertures between the parallel strips can be varied as desired. Also, the holes formed in one or both marginal positions of the releasable backing may take any of numerous different shapes or configurations, or may be spaced relative to each other in any of numerous different patterns corresponding to or otherwise dictated by the patterns of the feed pins or like drive members of the manufacturing equipment. Accordingly, this detailed description of preferred embodiments is to be taken in an illustrative as opposed to a limiting sense.

What is claimed is:

1. A marking grid for use in radiographic imaging, comprising:

a substrate, the substrate having a front side and a back side, the back side being coated with a pressure sensitive adhesive;

a plurality of elongated, substantially parallel strips of material fixed to the front side of the substrate and spaced relative to each other, each strip being made from a material that is at least partially radiopaque; and a plurality of elongated apertures formed through the substrate between the strips, wherein a plurality of the elongated apertures extend laterally between adjacent strips and extend in the elongated direction of the strips along a substantial portion of the length of at least one adjacent strip.

2. The marking grid defined in claim 1, further comprising a releasable backing, and wherein the pressure sensitive adhesive on the back side of the substrate is releasably attached to the releasable backing.

3. The marking grid as defined in claim 2, wherein the releasable backing defines a plurality of apertures formed in a marginal portion thereof and spaced relative to each other in an elongated direction of the backing.

4. The marking grid as defined in claim 3, wherein the releasable backing defines a plurality of apertures formed in opposing marginal portions thereof and spaced relative to each other in an elongated direction of the backing.

5. The marking grid as defined in claim 2, wherein the releasable backing defines a gripping portion underlying and releasably secured to the substrate, and being separated from the remainder of the substrate along a periphery of the gripping portion to thereby allow the gripping portion to be removed with the substrate from the remainder of the backing.

6. The marking grid as defined in claim 5, wherein the gripping portion underlies and is releasably secured to a corner portion of the substrate.

7. The marking grid as defined in claim 1, wherein the strips are comprised of particles dispersed in at least one of a hot melt and a glue.

8. The marking grid as defined in claim 7, wherein the particles are comprised of at least one of tungsten and bismuth.

9. The marking grid as defined in claim 8, wherein the metal wire is fixedly secured to the substrate by a glue.

10. The marking grid as defined in claim 7, wherein the particles are comprised of at least one of barium sulfate and calcium carbonate.

11. The marking grid as defined in claim 7, wherein the particles are comprised of a substance with a density greater than 1 g/cm$^3$.

12. The marking grid as defined in claim 1, wherein the strips are comprised of metal wire.

13. The marking grid as defined in claim 1, wherein the strips are comprised of a homogeneous non-metallic material.

14. The marking grid as defined in claim 1, wherein the strips are comprised of polyvinyl chloride.

15. The marking grid as defined in claim 1, wherein the strips are comprised of a plastic material compounded with a metal.

16. The marking grid as defined in claim 13 or 15, wherein the strip is fixedly secured to the substrate by a glue.

17. The marking grid as defined in claim 1, wherein the strips are comprised of nylon filled with tungsten carbide.

18. The marking grid as defined in claim 1, wherein the substrate is an elastic material.

19. The marking grid as defined in claim 1, wherein the elastic material is capable of stretching between approximately 5% and approximately 50% of its original dimensions without rupture.

20. The marking grid as defined in claim 1, wherein each elongated aperture extends along substantially the entire length of at least one adjacent strip.

21. The marking grid as defined in claim 1, wherein at least one elongated aperture is wider than a plurality of the other elongated apertures to facilitate locating the marking grid on a radiographic image.

22. A marking grid for use in radiographic imaging, comprising:
a substrate defining a front side and a back side;
first means superimposed over the back side of the substrate for releasably attaching the substrate to a patient's skin;
a plurality of second means fixedly secured on the front side of the substrate and formed of a material that is at least partially radiopaque for marking a patient's skin on a radiographic image, wherein the plurality of second means are laterally spaced relative to each other and extend in an elongated direction from approximately one side of the substrate to the other; and
a plurality of third means formed through the substrate between the second means and extending in the elongated direction along a substantial portion of the length of at least one adjacent second means for permitting at least one of a marking instrument and a biopsy instrument to be inserted therethrough onto the patient's skin underlying the marking grid.

23. The marking grid as defined in claim 22, wherein the first means is defined by a pressure sensitive adhesive coating on the back side of the substrate.

24. The marking grid as defined in claim 22, wherein each second means is defined by a strip of at least partially radiopaque material mounted on the front side of the substrate.

25. The marking grid as defined in claim 24, wherein the plurality of strips are laterally spaced and approximately parallel relative to each other.

26. The marking grid as defined in claim 22, wherein each third means is defined by an elongated aperture formed through the substrate adjacent to at least one respective second means, and a plurality of the elongated apertures extend laterally between the second means and extend in the elongated direction of the second means along a substantial portion of the length of the at least one adjacent second means.

27. The marking grid as defined in claim 26, wherein each elongated aperture extends along substantially the entire length of at least one adjacent second means.

28. The marking grid as defined in claim 22, further comprising a releasable backing secured to the first means on the back side of the substrate.

29. The marking grid as defined in claim 28, further comprising means releasably secured to the back side of the substrate for gripping the substrate and facilitating removal of the substrate from the releasable backing.

30. The marking grid as defined in claim 22, wherein the releasable backing includes fourth means formed in at least one marginal portion thereof for registering the marking grid with at least one tool for manufacturing the marking grid.

31. The marking grid as defined in claim 30, wherein the fourth means is defined by a plurality of apertures spaced relative to each other in an elongated direction of the backing along at least one marginal portion thereof.

32. The marking grid as defined in claim 22, further comprising means for allowing the substrate to elastically deform with movement of the patient's skin releasably attached thereto.

33. The marking grid as defined in claim 32, wherein the means for allowing elastic deformation includes an elastic material forming the substrate.

34. The marking grid as defined in claim 22, wherein a plurality of second means are approximately equidistantly spaced relative to each other, and at least one other second means is laterally spaced relative to at least one other adjacent second means a different distance to facilitate locating the marking grid on a radiographic image.

* * * * *

UNITED STATES PATENT AND TRADEMARK OFFICE
CERTIFICATE OF CORRECTION

PATENT NO. : 6,714,628 B2
DATED : March 30, 2004
INVENTOR(S) : Mark Broyles, Hermann Kasper and Kimberlee Olson It is certified that error appears in the above-identified patent and that said Letters Patent is hereby corrected as shown below:

<u>Title page, Item [54], and Column 1, Lines 2 and 3,</u>
Title delete,
"AND METHOD OF MAKING SUCH A GRID" title should read -- MARKING GRID FOR RADIOGRAPHIC IMAGING --.

Signed and Sealed this

Twenty-ninth Day of June, 2004

JON W. DUDAS
*Acting Director of the United States Patent and Trademark Office*